(12) United States Patent
Couteau et al.

(10) Patent No.: US 6,566,886 B1
(45) Date of Patent: May 20, 2003

(54) METHOD OF DETECTING CRYSTALLINE DEFECTS USING SOUND WAVES

(75) Inventors: Terri A. Couteau, Rosanky, TX (US); Michael J. Satterfield, Round Rock, TX (US); Laura A. Pressley, Austin, TX (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 28 days.

(21) Appl. No.: 09/819,785

(22) Filed: Mar. 28, 2001

(51) Int. Cl.[7] .............................................. G01R 31/08
(52) U.S. Cl. ......................................... 324/514; 73/579
(58) Field of Search ........................... 324/514; 73/579, 73/582; 134/1

(56) References Cited

U.S. PATENT DOCUMENTS

| | | | |
|---|---|---|---|
| 4,931,411 A | 6/1990 | Tigelaar et al. ............. 437/192 |
| 5,714,413 A | 2/1998 | Brigham et al. ............. 438/301 |
| 5,726,087 A | 3/1998 | Tseng et al. ................. 438/261 |
| 5,858,104 A | * 1/1999 | Clark ............................. 134/1 |
| 5,863,820 A | 1/1999 | Huang ........................ 438/241 |
| 5,872,046 A | 2/1999 | Kaeriyama et al. ......... 438/465 |
| 6,027,971 A | 2/2000 | Cho et al. .................... 438/257 |
| 6,039,814 A | 3/2000 | Ohmi et al. ..................... 134/1 |
| 6,063,696 A | 5/2000 | Brenner et al. ............. 438/465 |

FOREIGN PATENT DOCUMENTS

| | | | |
|---|---|---|---|
| DE | 44 02 230 | * 1/1995 | |
| JP | 60 196930 | 2/1986 | ............ H01L/21/02 |
| WO | WO 00 19511 A | 4/2000 | ......... H01L/21/336 |

OTHER PUBLICATIONS

Aaron Levinson; *Sonoluminescence Overview and Future Applications* (http://starfire.ne.uiuc.edu/–ne201/1995/levinson/sonulum.html); pp. 1–7; Nov. 19, 1995.

Bruno Gompf; *Studying Bubble Collapse on a Subnanometer Time Scale* (http://www.acoustics.org/137th/gompf.html +ca) pp. 1–3; Mar. 15, 1999.

Joachim Holzfuss et al.; *Shock Wave Emissions of a Sonoluminescencing Bubble* (http://www.physik.tu–darmstadt.de/–hofu/paper/shock/main.html); pp. 1–7; 1998.

Terri Couteau et al.; *Dilute RCA Cleaning Chemistries* (http://www.semiconductor.net/semiconductor/issues/Issues/1998/oct98/docs/features4.asp); pp. 1–6; Oct 1, 1998.

Hideo Miura et al.; *Mechanical Stress Simulation for Highly Reliable Deep–Submicron Devices*; IEICE Trans. Electron; vol. E82, No. 6; Jun. 1999 & pp. 830–838.

* cited by examiner

Primary Examiner—Christine K. Oda
(74) Attorney, Agent, or Firm—Timothy M. Honeycutt

(57) ABSTRACT

Various methods of inspecting circuit structures are provided. In one aspect, a method of detecting structural defects in a circuit structure is provided. A natural frequency of the circuit structure is determined and the circuit structure is immersed in a liquid. A first plurality of sonic pulses is sent through the liquid. The first plurality of sonic pulses have a first frequency range selected to produce a plurality of collapsing bubbles proximate the circuit structure. The collapsing bubbles produce a second plurality of sonic pulses that have a second frequency range near or including the natural frequency of the circuit structure whereby the second plurality of sonic pulses causes the circuit structure to resonate. Thereafter, the circuit structure is inspected for structural damage. Early identification of crystalline defects is facilitated.

21 Claims, 2 Drawing Sheets

METHOD OF DETECTING CRYSTALLINE DEFECTS USING SOUND WAVES

BACKGROUND OF THE INVENTION

1. Field of the Invention

This invention relates generally to semiconductor processing, and more particularly to methods of inspecting circuit structures for structural defects using forced vibration thereof via sonic pulses.

2. Description of the Related Art

Accurate and reliable defect inspection is vital to successful modern integrated circuit fabrication. Many current integrated circuits now routinely contain millions of individual transistors, resistors and other types of circuit components. The patterning of just a few such components on a given circuit may involve scores or even hundreds of different process and wafer movement steps. Therefore, it is desirable to identify defective structural components and fabrication processes so that defective parts may be reworked or scrapped and process recipes adjusted as necessary. Because the processing of an integrated circuit proceeds in a generally linear fashion, that is, various steps are usually performed in a specific order, it is desirable to be able to identify the locations of defects as early in a semiconductor process flow as possible. In this way, defective parts may be identified so that they do not undergo needless additional processing.

The types of structural defects observed in semiconductor circuit structures are legion. One such example is catastrophic structural failure in patterned polysilicon lines. Such patterned structures are used for transistor gate electrodes, local interconnect structures, and power rails to name just a few. The failure mechanisms for such structures vary, and often include an actual rip-out or breaking away of the structure. The origins of such failures may be traced to film contamination, unintended void formation or crystalline defects. Structural weakness in the film due to any of these mechanisms may result in structural failure during processing steps that impart stresses to the wafer, such as thermal shocks associated with bath processes, chemical mechanical polishing, and plasma etching to name just a few.

Conventional techniques for identifying structural defects usually rely on some type of imaging of the structure of interest. Techniques such as optical microscopy, scanning electron microscopy and x-ray diffraction are useful in identifying certain types of structural defects. However, the latter two techniques are generally destructive of the circuit structure and thus require test wafers or sacrifice of the tested wafer, and neither of the three can pick up some types of highly localized or otherwise obscured crystalline defects. These more latent types of defects may not reveal themselves until the integrated circuit is stressed thermally or otherwise much later in a process flow.

The present invention is directed to overcoming or reducing the effects of one or more of the foregoing disadvantages.

SUMMARY OF THE INVENTION

In accordance with one aspect of the present invention, a method of detecting structural defects in a circuit structure is provided. A natural frequency of the circuit structure is determined and the circuit structure is immersed in a liquid. A first plurality of sonic pulses is sent through the liquid. The first plurality of sonic pulses have a first frequency range selected to produce a plurality of collapsing bubbles proximate the circuit structure. The collapsing bubbles produce a second plurality of sonic pulses that have a second frequency range near or including the natural frequency of the circuit structure whereby the second plurality of sonic pulses causes the circuit structure to resonate. The circuit structure is inspected for structural damage.

In accordance with another aspect of the present invention, a method of inspection is provided that includes determining a natural frequency of a polysilicon line structure and immersing the polysilicon line structure in a liquid. A first plurality of sonic pulses is sent through the liquid. The first plurality of sonic pulses have a first frequency range selected to produce a plurality of collapsing bubbles proximate the polysilicon line structure. The collapsing bubbles produce a second plurality of sonic pulses that have a second frequency range near or including the natural frequency of the polysilicon line structure whereby the second plurality of sonic pulses causes the polysilicon line structure to resonate. The polysilicon line structure is inspected for structural damage.

In accordance with another aspect of the present invention, a method of inspection is provided that includes determining a natural frequency of a trench structure in a substrate and placing the substrate in a liquid so that at least the trench structure is immersed therein. A first plurality of sonic pulses is sent through the liquid. The first plurality of sonic pulses has a first frequency range selected to produce a plurality of collapsing bubbles proximate the trench structure. The collapsing bubbles produce a second plurality of sonic pulses that have a second frequency range near or including the natural frequency of the trench structure whereby the second plurality of sonic pulses causes the trench structure to resonate. The trench structure is inspected for structural damage.

BRIEF DESCRIPTION OF THE DRAWINGS

The foregoing and other advantages of the invention will become apparent upon reading the flowing detailed description and upon reference to the drawings in which.

DETAILED DESCRIPTION OF SPECIFIC EMBODIMENTS

Figure 1:
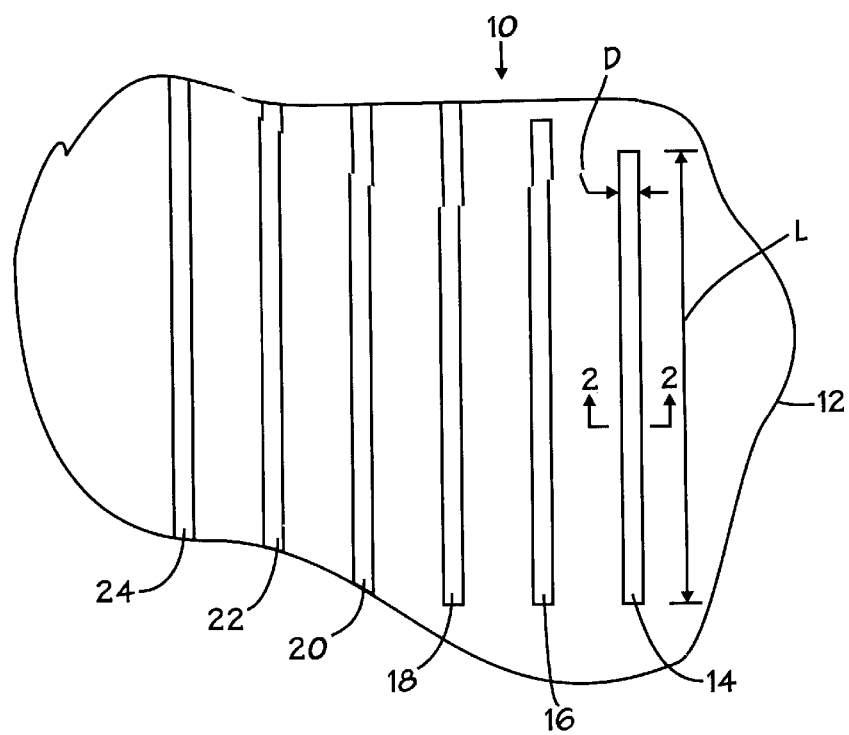
FIG. 1 is a plan view of a small portion of an integrated circuit patterned on a semiconductor substrate in accordance with the present invention.

In the drawings described below, reference numerals are generally repeated where identical elements appear in more than one figure. FIG. 1 is a plan view of a small portion of an integrated circuit 10 patterned on a semiconductor substrate 12 in accordance with the present invention. A plurality of conductor lines 14, 16, 18, 20, 22 and 24 are shown and may be patterned as transistor gate electrodes, interconnect lines, or other types of conducting structures frequently used in semiconductor fabrication. Depending upon the requirements of the integrated circuit 10, the conductor lines 14, 16, 18, 20, 22 and 24 may be patterned with a variety of lengths. For example, the conductor line 14 may be fabricated with a length L. The width D of the conductor line 14 may be the minimum feature size for the available process technology or some dimension larger than that as desired. The detailed structure of the conductor line 14 may be understood by referring now also to FIG. 2, which is a cross-sectional view of FIG. 1 taken at section 2—2. An insulating film 26 is formed directly on the substrate 12 and is thus interposed between the conductor line 14 and the substrate 12. This insulating film 26 is customarily a gate dielectric film or a pad oxide layer. The conductor line 14 may be composed of virtually any of a large variety of materials commonly used for integrated circuit conductor structures, such as, for example, polysilicon, amorphous silicon, aluminum, copper, titanium, titanium nitride, tungsten or the like. For the purpose of the present illustration, the conductor structure 14 is composed of polysilicon.

As the skilled artisan will appreciate, crystalline structures, such as the conductor structure 14, may be fabricated with or later develop crystalline defects that substantially reduce the structural integrity of the structure 14. The origins of such defects are legion, and include weak grain boundaries, crystal lattice damage due to impurity implants, impurity contamination, or thermal stresses. The effect is not limited to the conductor structure 14. Indeed, the same types of structural defects may appear in the substrate 12 as well. An exemplary crystalline defect 28 is shown in the conductor structure 14 and another exemplary crystalline defect 30 is shown positioned in the substrate 12 below the conductor structure 14. The defects 28 and 30 represent areas that are prone to structural failure during subsequent processing of the substrate 12. The substrate 12 undergoes a multitude of different processing steps toward the completion of the integrated circuit 10. These processes include, for example, chemical mechanical polishing, various etches, high temperature anneals, and sonic cleaning steps.

Figure 2:
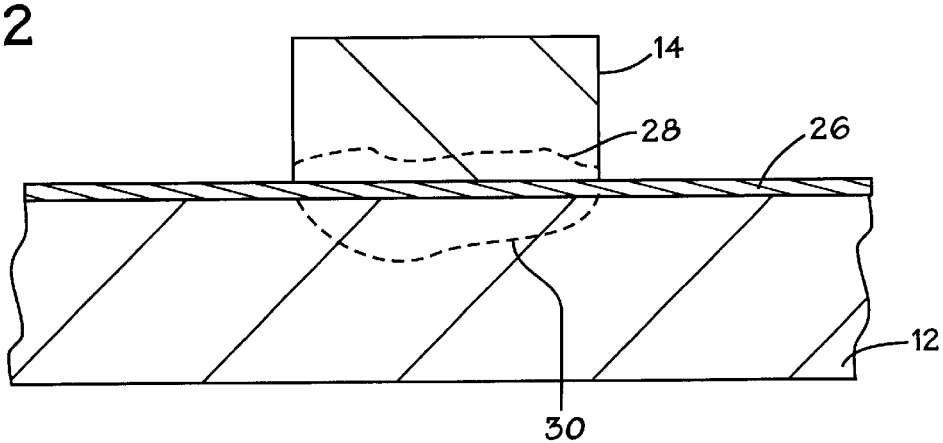
FIG. 2 is a cross-sectional view of the substrate of FIG. 1 taken at section 2—2.
Figure 3:
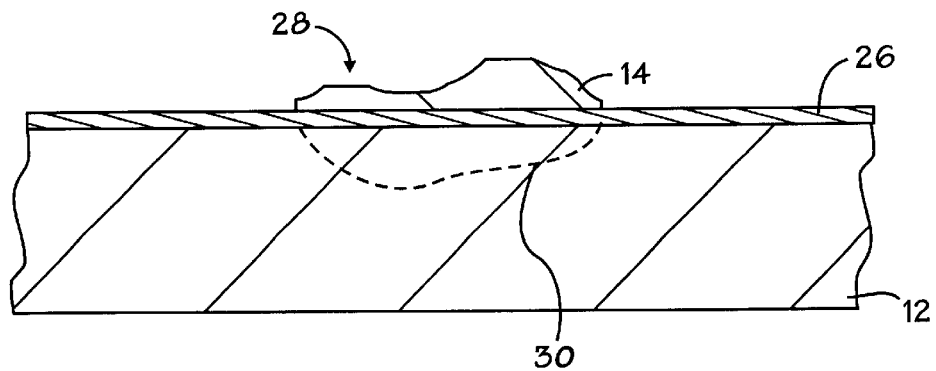
FIG. 3 is the cross-sectional view of FIG. 2 depicting one potential mode of structural failure of a portion of the integrated circuit.
Figure 4:
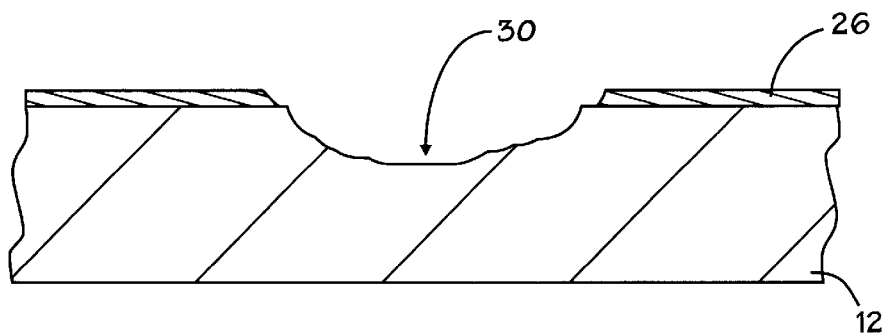
FIG. 4 is a cross-sectional view like FIG. 3 depicting another potential mode of structural of portion of the integrated circuit.

Two exemplary failure mechanisms for the conductor structure 14 are depicted in FIGS. 3 and 4, which are cross-sectional views like FIG. 2. Turning first to FIG. 3, the conductor structure 14 has fractured along the defect 28 and essentially ripped away from the remaining portion of the conductor structure 14. Another type of structural failure is depicted in FIG. 4 wherein the entire conductor structure 14 rips away along with a portion of the substrate 12 due to structural failure along the defect 30.

Figure 5:
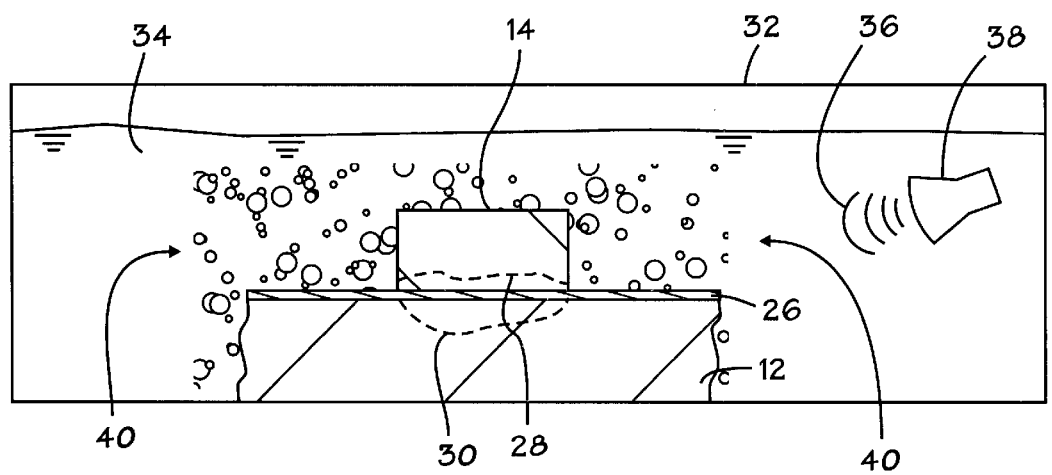
FIG. 5 is a side view of a liquid bath suitable for producing vibrations in the integrated circuit of FIG. 1 by sonic pulse propagation in accordance with the present invention.

It is desirable to be able to identify the locations of the defects 28 and 30 as early in a semiconductor process flow as possible. In this way, defective parts may be identified so that they do not undergo needless processing that may ultimately result in the types of catastrophic structural failures depicted in FIGS. 3 and 4. An exemplary method in accordance with the present invention for locating defects, such as the defects 28 and 30, may be understood by referring now to FIGS. 1 and 5. As shown in FIG. 5, the substrate 12 may be immersed in a bath 32 containing a volume of a liquid 34 and subjected to a plurality of sonic pulses 36 from an acoustic source 38. The propagating wave fronts of the sonic pulses 36 strike the substrate 12 and the conductor structure 14 and reflect off. This sets up an interference pattern consisting of positive and destructive interference nodes. At those locations where destructive interference occurs, highly localized areas of low pressure, i.e., cavitation will occur, resulting in the formation of huge numbers of bubbles 40 in the liquid 34. When some of the bubbles 40 impact the surfaces of the conductor structure 14, they collapse, releasing small amounts of kinetic energy in the form of high frequency vibrations. By tuning the parameters of the sonic pulses 36 to the geometry and composition of the conductor structure 14, the bubbles 40 may be generated with a selected collapse period that initiates resonance in the conductor structure 14. The resonance condition will cause structural failure either at the defect 28 or the defect 30 or both. In this way, those structures having defects, such as the defects 28 and 30, may be readily identified so that the substrate 12 does not undergo unnecessary additional processing. The vibration characteristics of the conductor structure 14 may be modeled mathematically in the first instance as a vibrating spring with a spring mass damper. If the structure 14 is subjected to a time-varying input force P sin ωt, which corresponds to the input pulses from the collapsing bubbles 40, the equation of motion for the structure 14 is given by:

$$m\ddot{x}+c\dot{x}+kx=P\sin\omega t \qquad \text{Equation 1}$$

where x is the displacement of an arbitrarily selected point on the conductor structure 14 from an equilibrium position. In Equation 1, k is the spring constant of the conductor structure 14, m is the mass of the conductor structure 14, c is the actual damping value and ω is the frequency of the input force, that is, the frequency of the pulses generated by the collapsing bubbles 40. Note that the expression P sin ωt for the time-varying input force of the collapsing bubbles 40 represents an approximation of the actual input force. A Fourier series will provide a more exact representation of the time-varying input force resulting from the combined action of hundreds of thousands or even millions of the collapsing bubbles 40. However, Equation 1 provides a useful approximation to illustrate the present invention.

By performing a Laplace transform on Equation 1, a subsequent algebraic solution thereof, and a follow up inverse Laplace transform, a solution of Equation 1 becomes:

$$x(t) = \frac{P}{\sqrt{(k-m\omega^2)^2 + c^2\omega^2}}\sin\left(\omega t - \tan^{-1}c\frac{\omega}{k-m\omega^2}\right) \qquad \text{Equation 2}$$

The damped natural frequency $\omega_n$ of the structure 14 is given by:

$$\omega_n = \sqrt{\frac{k}{m} - \frac{c^2}{4m^2}} \qquad \text{Equation 3}$$

Equation 3 suggests that so long as the damping value c is greater than zero, the conductor 14 will not experience resonance. However, experiments on conductors 14 with lengths of 2.0 μm have suggested resonance induced structural failure. This suggests an under damped condition, that is, that the actual damping value c is quite small, so that Equation 2 yields large enough amplitude x(t) swings to produce failure.

One way to determine the natural frequency $\omega_n$ of the structure 14, and thus the desired input frequency to induce vigorous vibrations in the structure 14, is to assume that the structure 14 mimics the behavior of a stretched string. In such circumstances, the frequency of vibration in the structure 14 is given by the following equation:

$$v = \frac{n}{2l}\bar{v} \qquad \text{Equation 4}$$

where $v$ is the frequency of vibration, $l$ is the length of the conductor structure 14, $\bar{v}$ is the velocity of sound through the conductor structure 14 and n is the harmonic number, e.g., n=1 corresponds to the fundamental harmonic. The velocity of sound in the structure 14 may be determined using the following equation:

$$\bar{v} = \sqrt{\frac{Y}{\rho}} \qquad \text{Equation 5}$$

where Y is Young's modulus and $\rho$ is the density of the conductor structure 14. The velocity of sound through and the density $\rho$ of the conductor structure 14 will generally be well-known parameters, but may be determined experimentally if necessary.

Experiments were performed on polysilicon conductor structures 14 with conductor lengths l varying from less than 1.0 $\mu$m up to several $\mu$m. Structural failure was observed in conductor structures 14 with lengths l of 2.0 $\mu$m and longer. However, no failures were observed at lengths less than 2.0 $\mu$m. This suggests that the 2.0 $\mu$m length corresponds to a fundamental harmonic, e.g., n=1, resonant wavelength. Thus, substituting the values of Y, $\rho$ and l for the conductor structure 14 into Equation 5, yields a resonant frequency $v$ of about 2.0 GHz. Thus, if the input frequency $\omega$ corresponding to the collapsing of the bubbles 40 is about 2.0 GHz, a resonance condition will be initiated in the structure 14. A resonant frequency of 2 GHz corresponds to a pulse period of about 500 picoseconds.

The collapse time for the bubbles 40 will depend upon a number of parameters associated with the liquid 34, and the sonic pulses 36. The experiments on the 2.0 $\mu$m conductors 14 demonstrated that sonic pulses 36 generated with a frequency range of about 950 kHz to 1.5 MHz, and power of about 10 to 300 Watts in the liquid 34 consisting of ultra pure water at a temperature of about 25° C. will produce bubbles 40 with collapse times in a range of 100 to 500 picoseconds. This collapse time range corresponds to a frequency range of about 10.0 to 2.0 GHz, which is suitable to initiate resonance or near resonance vibrations in the conductor 14. While it is desirable for the frequency range of the sonic pulses generated by the collapsing bubbles 40 to encompass the natural frequency $\omega_n$ of the conductor structural 14, it is also anticipated that the conductor structure 14 will undergo rigorous forced vibration where the frequency range is at or near the natural frequency $\omega_n$.

The sonic pulsing of the conductor structure 14 may be combined with a cleansing bath to remove contaminants or other residues. Indeed, similar diagnostic results may be obtained where the liquid 34 consists of less than 50% solutions of acid or basic solutions, such as HCl or $NH_4OH$. Such acid or base solutions may contain up to about 50% by volume $H_2O_2$.

As noted above, structural failure was observed in lines having a minimum length of 2.0 $\mu$m. Interestingly, structure failures were observed in other lines that had lengths that were integer multiples of 2.0 $\mu$m, that is 4.0 and 6.0 $\mu$m. This is thought to indicate that the polysilicon lines 14, 16, 18, 20, 22 and 24 (See FIG. 1) are undergoing resonance and second and third harmonics in response to bubble collapse times of about 100 to 500 picoseconds.

Following the sonic treatment of the integrated circuit 10, one or more inspections for structural failures may be performed. The inspection may be by optical microscopy, scanning electron microscopy, infrared scanning, laser scanning or other well-known morphology determination techniques. Indeed any of the above techniques may be performed in concert if desired.

Figure 6:
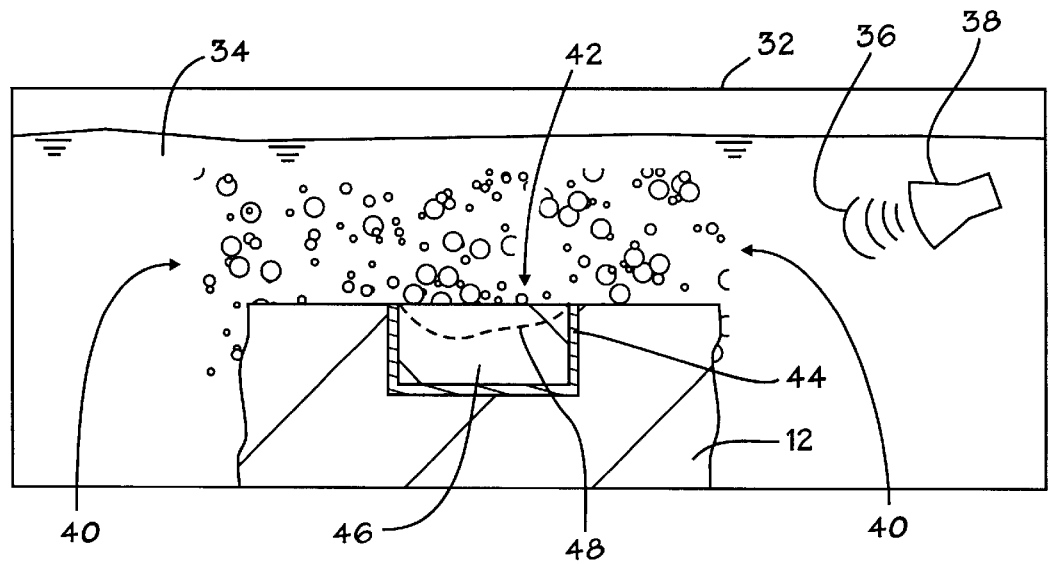
FIG. 6 is a side view like FIG. 5 depicting the production of vibrations in a trench structure by sonic pulse propagation in accordance with the present invention.

In the foregoing illustrative embodiment, a structure fabricated on the substrate 12 is subjected to selective sonic pulses in order to initiate a resonance condition in the structure 14. The methodology may be applied to other than above-substrate structures. FIG. 6 illustrates just one possible example of use of the technique in accordance with the present invention in order to root out defects in other types of integrated circuit structures. FIG. 6 depicts the substrate 12 in which a trench structure 42 is formed. The trench structure 42 may consist of a liner layer 44 capped with a bulk material 46. Such a structure may be, for example, a trench-based conductor structure or isolation structure as desired. For the purposes of the present illustration, the structure 42 is a trench-based polysilicon conductor structure wherein the liner film 44 is composed of oxide and the bulk material 46 is composed of doped polysilicon. Again, for the purpose of the present illustration, it is assumed that the polysilicon material 46 has an internal defect 48 of the type described above. As with the foregoing illustrative embodiment, the substrate 12 may be immersed in the bath 32 and subjected to a plurality of sonic pulses 36 from the acoustic source 38 that propagate through the liquid 34. The same general procedure outlined above may be used to tailor the parameters of the input sonic pulses 36 in order to achieve a desirable input impulse frequency of the collapsing bubbles 40 to initiate a resonance condition in the trench structure 42. Visual inspection may follow the sonic bath.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A method of detecting structural defects in a circuit structure, comprising:

determining a natural frequency of the circuit structure;

immersing the circuit structure in a liquid;

sending a first plurality of sonic pulses through the liquid, the first plurality of sonic pulses having a first frequency range selected to produce a plurality of collapsing bubbles proximate the circuit structure, the collapsing bubbles producing a second plurality of sonic pulses having a second frequency range near or including the natural frequency of the circuit structure whereby the second plurality of sonic pulses causes the circuit structure to resonate; and inspecting the circuit structure for structural damage.

2. The method of claim 1, wherein the inspecting of the circuit structure comprises electron microscopy.

3. The method of claim 1, wherein the inspecting of the circuit structure comprises optical microscopy.

4. The method of claim 1, wherein the liquid comprises water.

5. The method of claim 1, wherein the liquid comprises a solution of water and ammonium hydroxide or hydrochloric acid.

6. The method of claim 1, wherein the liquid comprises a solution of ammonium hydroxide and hydrogen peroxide in water.

7. The method of claim 1, wherein the determination of the natural frequency of the circuit structure comprises determining a length l of the circuit structure, a speed of sound $\bar{v}$ through the circuit structure and a density $\rho$ of the circuit structure, and solving for the natural frequency $v$ according to the below equations where Y is Young's Modulus:

$$v = \frac{n}{2l}\bar{v};$$

and $$\bar{v} = \sqrt{\frac{Y}{\rho}}.$$

8. A method of inspection, comprising:
 determining a natural frequency of a polysilicon line structure;
 immersing the polysilicon line structure in a liquid;
 sending a first plurality of sonic pulses through the liquid, the first plurality of sonic pulses having a first frequency range selected to produce a plurality of collapsing bubbles proximate the circuit structure, the collapsing bubbles producing a second plurality of sonic pulses having a second frequency range near or including the natural frequency of the polysilicon line structure whereby the second plurality of sonic pulses causes the polysilicon line structure to resonate; and
 inspecting the polysilicon line structure for structural damage.

9. The method of claim 8, wherein the inspecting of the polysilicon line structure comprises electron microscopy.

10. The method of claim 8, wherein the inspecting of the polysilicon line structure comprises optical microscopy.

11. The method of claim 8, wherein the liquid comprises water.

12. The method of claim 8, wherein the liquid comprises a solution of water and ammonium hydroxide or hydrochloric acid.

13. The method of claim 8, wherein the liquid comprises a solution of ammonium hydroxide and hydrogen peroxide in water.

14. The method of claim 8, wherein the determination of the natural frequency of the polysilicon line structure comprises determining a length l of the polysilicon line structure, a speed of sound $\bar{v}$ through the polysilicon line structure and a density $\rho$ of the polysilicon line structure, and solving for the natural frequency $v$ according to the below equations where Y is Young's Modulus:

$$v = \frac{n}{2l}\bar{v};$$

and $$\bar{v} = \sqrt{\frac{Y}{\rho}}.$$

15. A method of inspection, comprising:
 determining a natural frequency of a trench structure in a substrate;
 placing the substrate in a liquid so that at least the trench structure is immersed therein;
 sending a first plurality of sonic pulses through the liquid, the first plurality of sonic pulses having a first frequency range selected to produce a plurality of collapsing bubbles proximate the trench structure, the collapsing bubbles producing a second plurality of sonic pulses having a second frequency range near or including the natural frequency of the trench structure whereby the second plurality of sonic pulses causes the trench structure to resonate; and
 inspecting the trench structure for structural damage.

16. The method of claim 15, wherein the inspecting of the trench structure comprises electron microscopy.

17. The method of claim 15, wherein the inspecting of the trench structure comprises optical microscopy.

18. The method of claim 15, wherein the liquid comprises water.

19. The method of claim 15, wherein the liquid comprises a solution of water and ammonium hydroxide or hydrochloric acid.

20. The method of claim 15, wherein the liquid comprises a solution of ammonium hydroxide and hydrogen peroxide in water.

21. The method of claim 15, wherein the determination of the natural frequency of the trench structure comprises determining a length l of the trench structure, a speed of sound $\bar{v}$ through the trench structure and a density $\rho$ of the trench structure, and solving for the natural frequency $v$ according to the below equations where Y is Young's Modulus:

$$v = \frac{n}{2l}\bar{v};$$

and $$\bar{v} = \sqrt{\frac{Y}{\rho}}.$$

* * * * *